(12) United States Patent
Carroll et al.

(10) Patent No.: US 10,150,843 B2
(45) Date of Patent: Dec. 11, 2018

(54) PROCESS FOR LIQUEFACTION OF LIGNOCELLULOSIC BIOMASS

(71) Applicant: Georgia-Pacific LLC, Atlanta, GA (US)

(72) Inventors: Michael E. Carroll, Loganville, GA (US); Johannes A. Kroon, Heerlen (NL); Rudy F. M. J. Parton, Winkelse (BE); Subrata Sen, Kennesaw, GA (US); Pierre L. Woestenborghs, Dilsen (BE)

(73) Assignee: Georgia-Pacific LLC, Atlanta, GA (US)

( * ) Notice: Subject to any disclaimer, the term of this patent is extended or adjusted under 35 U.S.C. 154(b) by 8 days.

(21) Appl. No.: 15/558,362

(22) PCT Filed: Mar. 16, 2016

(86) PCT No.: PCT/US2016/022539
§ 371 (c)(1),
(2) Date: Sep. 14, 2017

(87) PCT Pub. No.: WO2016/149300
PCT Pub. Date: Sep. 22, 2016

(65) Prior Publication Data
US 2018/0094104 A1    Apr. 5, 2018

Related U.S. Application Data

(60) Provisional application No. 62/134,221, filed on Mar. 17, 2015.

(51) Int. Cl.
| | |
|---|---|
| *C08B 1/00* | (2006.01) |
| *C08H 8/00* | (2010.01) |
| *C07C 51/43* | (2006.01) |
| *C08B 15/08* | (2006.01) |
| *C08B 37/00* | (2006.01) |
| *C08B 37/14* | (2006.01) |

(52) U.S. Cl.
CPC ............. *C08H 8/00* (2013.01); *C07C 51/43* (2013.01); *C08B 1/00* (2013.01); *C08B 15/08* (2013.01); *C08B 37/0057* (2013.01); *C08B 37/14* (2013.01)

(58) Field of Classification Search
CPC ................................. C08H 8/00; C07C 51/43
USPC ........................................................ 562/577
See application file for complete search history.

(56) References Cited

U.S. PATENT DOCUMENTS

| | | | | |
|---|---|---|---|---|
| 2014/0170713 A1* | 6/2014 | Retsina | ................... | C13K 1/02 435/99 |
| 2015/0052806 A1* | 2/2015 | Frey | ....................... | C07C 51/42 44/606 |

FOREIGN PATENT DOCUMENTS

| | | |
|---|---|---|
| WO | 2011/141545 | 11/2011 |
| WO | 2014/087016 | 6/2014 |

* cited by examiner

*Primary Examiner* — Deborah D Carr
(74) *Attorney, Agent, or Firm* — Ram W. Sabnis

(57) ABSTRACT

Methods and systems are provided for improved liquefaction of a lignocellulosic biomass. The methods include reacting a lignocellulosic biomass slurry at mild conditions for a short period to produce a first reaction mixture having a reduced viscosity as compared to the lignocellulosic biomass slurry and that is substantially free of levulinic acid and hydroxymethylfurfural. The methods further include separating the first reaction mixture into a solid fraction and a liquid fraction, the solid fraction having a majority of lignin from the lignocellulosic biomass slurry and the liquid fraction having a majority of hemicellulose and greater than about 30% by weight of cellulose from the lignocellulosic biomass slurry. The method advantageously prevents or eliminates the formation of tar and/or char.

20 Claims, No Drawings

PROCESS FOR LIQUEFACTION OF LIGNOCELLULOSIC BIOMASS

TECHNICAL FIELD

The present application relates to methods for liquefaction of a lignocellulosic biomass. In particular, the present application relates to a two-step process for the production of levulinic acid and lignin from a lignocellulosic biomass.

BACKGROUND

Levulinic acid is a starting molecule for the synthesis of chemicals useful in various applications, including fuel additives, plasticizers, and solvents. For example, levulinic acid can be used to synthesize methyl tetrahydrofuran (MTHF), delta-amino levulinic acid (used as herbicides and pesticides), diphenolic acid (used to synthesize polycarbonates), succinic acid (used to make polyesters), and gamma valerolactone (5-methylbutyrolactone) (used for production of adipic acid (1,6-hexanedioic acid)).

Levulinic acid can be produced by acid hydrolysis of C6 sugars, which is readily present in lignocellulosic biomass. Lignocellulosic biomass also includes C5 sugars, typically bound to hemicellulose, which can be converted to furfural, and lignin.

Prior art methods for production of levulinic acid from woody biomass, such as those described in U.S. Pat. No. 5,608,105 and U.S. Pat. No. 4,897,497, disclose a two-step hydrolysis process for the production of levulinic acid from woody biomass. For example, U.S. Pat. No. 5,608,105 discloses a first hydrolysis step carried out for a short period at relatively high temperature followed by a second hydrolysis step carried out for a longer period at lower temperatures. These and other prior art methods for production of levulinic acid, however, suffer from significant disadvantages.

For example, prior art methods of hydrolysis of lignocellulosic biomass result in the formation of large amounts of tar and char, materials that are insoluble in water and become viscous and very dark to almost black when concentrated. Tar usually refers to a viscous liquid formed from destructive heating of organic material, for example by pyrolysis, and when carbohydrates are subjected to acid hydrolysis, particularly at high temperatures. Char usually refers to solid material, for example the remains of solid biomass that has been incompletely combusted, such as charcoal if wood is incompletely burned.

The formation of tar and char that is abundant in prior art processes is undesirable. For example, the dark color of tar and char makes the product unattractive (i.e., from the perspective of the user or customer) and the presence of tar and char may negatively affect the performance of the final product.

Another disadvantage of prior art processes is that the lignin present in the lignocellulosic biomass ends up as char. Lignin is a heterogeneous polymer of aliphatic and aromatic portions which is present in all kinds of wood. In paper manufacture, due to the harsh conditions, pulped lignin has undergone considerable chemical modification and is generally a dark brown to black brittle solid, and is generally only suitable as fuel. Lignin as a fuel source gives it a low added value. There are other higher value applications, such as the manufacture of paper, food additives (vanillin essence), fine chemistry, metallurgy, and emulsifiers; however, such applications are impossible when the lignin is in the form of char.

Still other disadvantages of prior art processes are that they are not suitable for high concentrations of biomass, do not produce products with high concentrations of levulinic acid, and require subsequent separation processes to separate the levulinic acid.

Thus, there remains a need for improved methods for producing levulinic acid and other desirable products from lignocellulosic biomass.

SUMMARY

In one embodiment, a method is provided for liquefaction of a lignocellulosic biomass including providing a lignocellulosic biomass slurry having a mineral acid in an amount from about 1% by weight to about 6% by weight; reacting the lignocellulosic biomass slurry at a first temperature of about 150° C. to about 200° C. for a first reaction period of about 30 seconds to about 10 minutes to produce a first reaction mixture having a reduced viscosity as compared to the lignocellulosic biomass slurry and substantially free of levulinic acid and hydroxymethylfurfural; and separating the first reaction mixture into a solid fraction and a liquid fraction, the solid fraction including a majority of lignin from the lignocellulosic biomass slurry and the liquid fraction including greater than about 30% by weight of cellulose from the lignocellulosic biomass slurry.

In another embodiment, a method is provided for producing levulinic acid including the steps of providing a lignocellulosic biomass slurry having a mineral acid in an amount from about 1% by weight to about 6% by weight; heating the lignocellulosic biomass slurry to a temperature of about 150° C. to about 200° C. for first reaction period of about 30 seconds to about 10 minutes to produce a first reaction mixture having a reduced viscosity as compared to the lignocellulosic biomass slurry and substantially free of levulinic acid and hydroxymethylfurfural; separating the first reaction mixture into a solid fraction and a liquid fraction, the solid fraction having a majority of lignin from the lignocellulosic biomass slurry and a liquid fraction having greater than about 30% by weight of cellulose originally present in the lignocellulosic biomass slurry; and reacting the liquid fraction at a temperature of about 120° C. to about 200° C. for a second reaction period sufficient to produce a second reaction mixture including levulinic acid and formic acid.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Embodiments of the present application address the above-described needs by providing methods for liquefaction of lignocellulosic biomass. By separating the liquefied lignocellulosic biomass formed during a first reaction, the formation of char and/or tar in subsequent reactions is substantially reduced and/or eliminated.

In the following description, numerous specific details are given to provide a thorough understanding of embodiments. The embodiments can be practiced without one or more specific details, or with other methods, components, materials, and the like. In other instances, well known structures, materials, or operations are not shown or described in detail to avoid obscuring aspects of the embodiments.

Reference throughout the specification to "one embodiment," "an embodiment," or "embodiments" means that a particular feature, structure, or characteristic described in connection with the embodiment is included in at least one embodiment. Thus, the appearances of the phrases "in one embodiment" or "in an embodiment" in various places throughout the specification are not necessarily referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. As used herein, the terms "comprise," "comprising," "include," and "including" are intended to be open, non-limiting terms, unless the contrary is expressly indicated.

The term "about," as used herein, indicates the value of a given quantity can include quantities ranging within 10% of the stated value, or optionally within 5% of the value, or in some embodiments within 1% of the value, or in some embodiments within 0.1% of the value. For example, about 0.5 may include about 0.45 and 0.55, about 10 may include 9 and 11, about 1000 may include 900 to 1100.

Methods for liquefaction of lignocellulosic include providing a lignocellulosic biomass slurry comprising a mineral acid, reacting the lignocellulosic biomass slurry to produce a first reaction mixture, and separating the first reaction mixture into a solid fraction and a liquid fraction. The solid fraction comprises a majority of lignin from the lignocellulosic biomass slurry and the liquid fraction comprises a majority of hemicellulose and greater than about 30% by weight of cellulose from the lignocellulosic biomass slurry.

After separation, the liquid fraction and solid fraction may undergo separate reactions to produce levulinic acid, formic acid, and/or furfural. For example, the method may include reacting the liquid fraction at a temperature of about 120° C. to about 200° C. for a second reaction period sufficient to produce a second reaction mixture comprising levulinic acid, formic acid and furfural. In another embodiment, the method may include reacting the solid fraction at a temperature and for a third reaction period sufficient to produce a third reaction mixture comprising levulinic acid and formic acid.

In embodiments, the method may further include subjecting the lignocellulosic biomass to steam extraction prior to the first reaction to produce a solid fraction comprising cellulose and lignin (the "pre-treated lignocellulosic biomass") and a liquid fraction comprising a majority of hemicellulose from the lignocellulosic biomass. Other types of separation processes also may be used to remove a majority of hemicellulose from the lignocellulosic biomass, such as a high pressure hot water extraction process. Advantageously, the extraction allows for removal of a majority of hemicellulose present in the lignocellulosic biomass (e.g., greater than about 60%, greater than about 70%, greater than 80%, greater than 90%, or greater than 95%). Removal of a majority of the hemicellulose reduces the production of products and by-products during liquefaction of the lignocellulosic biomass, thereby substantially reducing the need for subsequent separation steps to isolate the various products. In addition, removal of a majority of the hemicellulose from the lignocellulosic biomass decreases the formation of char during liquefaction of the lignocellulosic biomass. Thus, in embodiments a pre-treated lignocellulosic biomass forms the biomass feed stream that is subjected to the first reaction while the liquid fraction can be used to produce furfural in yet another reaction.

Lignocellulosic Biomass

Suitable lignocellulosic biomass materials include one or more six carbon chain compound (C6) precursors. Examples of suitable lignocellulosic biomass materials include any biological materials comprising lignocellulose that include C6 precursors, such as wood from trees, wood chips, slash or hog fuel from wood tree processing, forest residue, straw, hay, chaff, grass, grain, corn, corn husk, weeds, starch, algae, tree bark, leaves, paper pulp, paper sludge, or lignocellulosic containing material of biological origin, such as dung.

If necessary, the particle size of the lignocellulosic biomass can be reduced before introduction into the reaction system. Any manner known to be suitable to a skilled person can be used to reduce the particle size or otherwise increase the surface area of the lignocellulosic biomass. Examples of such methods include crushing, grinding, milling, cutting, chipping, shredding, granulation, fibrillation, steam explosion, and any combination thereof.

Liquefaction Process

An embodiment of a method for liquefaction of lignocellulosic biomass includes providing a biomass feed stream to a first reactor and reacting the lignocellulosic biomass in the biomass feed stream to produce a first reaction mixture. In some embodiments, the biomass feed stream may be in the form of a slurry including the lignocellulosic biomass and water.

In the first reactor, the lignocellulosic biomass of the biomass feed stream reacts with one or more mineral acids to produce the first reaction mixture. The mineral acid may be added to the biomass feed stream with water (e.g., to form the slurry) or may be added directly to either the biomass feed stream or the first reactor (not shown). Non-limiting examples of suitable mineral acids include hydrochloric acid, nitric acid, phosphoric acid, sulfuric acid, and the like. According to embodiments, the mineral acid may be added to the biomass feed stream in an amount from about 1% to about 6% by weight of the biomass feed stream. For example, in an embodiment the mineral acid may be added to the biomass feed stream in an amount from about 2% to about 5% by weight or from about 3% to about 5% by weight. In an embodiment, the mineral acid may be formed from a precursor, such as sulfur dioxide, added to the biomass feed stream.

The first reaction results in liquefaction of at least a portion of the lignocellulosic biomass to produce a first reaction mixture having a reduced viscosity as compared to the slurry of lignocellulosic biomass in the biomass feed stream. The first reaction mixture desirably is substantially free of levulinic acid and hydroxymethylfurfural (HMF). As used herein, "substantially free" means the composition has less than 1% by weight HMF and/or levulinic acid.

The first reaction mixture produced in the first reaction is separated into a solid fraction and a liquid fraction, the solid fraction comprising a majority of lignin from the lignocellulosic biomass slurry and the liquid fraction comprising a majority of hemicellulose and greater than about 30% by weight of cellulose from the lignocellulosic biomass. As used herein, the term "majority" means the composition has greater than about 50% by weight of the component than was present in the lignocellulosic biomass (e.g., greater than about 55%, 60%, 65%, 70%, 75%, 80%, 85%, 90%, or 95% by weight).

In embodiments, the timing for separating the liquid and solid components of the first reaction mixture may be determined by evaluating the dry matter content and/or viscosity of the first reaction mixture. For example, in one embodiment the step of separating the first reaction mixture occurs when the amount of dry matter in the first reaction mixture is substantially minimized.

In another embodiment, step of separating occurs when the amount of dry matter in the first reaction mixture has decreased to approximately 50% of the initial dry matter content (i.e., the amount of dry matter in the lignocellulosic biomass of the biomass feed stream before the first reaction). Generally, the dry matter content will initially decrease rapidly in the first reaction. The dry matter content will further decrease as the first reaction proceeds; however, this rate of decrease will become slower until the dry matter content reaches a dip, after which the dry matter content will increase, probably due to formation of char. Thus, in embodiments the step of separating the first reaction mixture is performed just before this dip is reached.

In yet another embodiment, the step of separating the first reaction mixture occurs when the viscosity of the first reaction mixture has decreased such that it is readily pumpable and/or stirrable. This can be determined by visual inspection (e.g., by watching the behavior of the slurry in the reactor) or by measuring the viscosity (e.g., torque) of the first reaction mixture.

In a preferred embodiment, the step of separating the first reaction mixture is initiated when both the viscosity of the first reaction mixture has substantially reached a minimum and just before the dry matter content has reached a dip. In other embodiments, the step of separating may be initiated before or after this moment (e.g., 10 seconds earlier or 20 seconds later).

The reaction parameters for the first reaction preferably are relatively mild conditions and for a short reaction period. If the temperature were too high, it would be more difficult to cool the reaction and the reaction would proceed too fast, resulting in undesirable char formation. However, if the temperature were too low (<150° C.), the desired decrease in viscosity would not occur, making subsequent solid-liquid separations difficult or even impossible. Thus, in embodiments the first reaction in the first reactor is performed at a first reaction temperature from about 150° C. to about 200° C., from about 160° C. to about 195° C., or from about 165° C. to about 190° C. for a first reaction period of about 30 seconds to about 10 minutes, from about 60 seconds to about 5 minutes, or from about 60 seconds and 120 seconds.

Those skilled in the art will understand that the temperature and the reaction period are dependent on one another. For example, at lower temperatures the first reaction period will be longer, whereas at higher temperatures the first reaction period will be shorter. Thus, in an exemplary embodiment the first reaction is at a first reaction temperature of about 180° C. to about 190° C. for a first reaction period of from about 60 seconds to about 120 seconds (e.g., 80 seconds, 90 seconds, or 100 seconds). Such reactions may be conducted in any suitable vessel, such as a pulp digester, that can provide shorter reaction times.

After separating the solid and liquid fractions of the first reaction mixture, the method may further include reacting the liquid fraction in a second reaction and/or reacting the solid fraction in a third reaction. For example, in an embodiment the liquid fraction may be reacted at a temperature of about 120° C. to about 200° C. for a second reaction period sufficient to produce a second reaction mixture comprising levulinic acid, formic acid and/or furfural. The second reaction period may be from about 60 minutes to about 120 minutes. Similarly, in an embodiment, the solid fraction may be reacted at a temperature and for a third reaction period sufficient to produce a third reaction mixture comprising levulinic acid and formic acid. The third reaction period may be from about 75 to about 150 minutes.

When processing lignocellulosic biomass, such as wood chips, the structure of the lignocellulosic biomass prevents use of high concentrations of biomass in the biomass slurry. At higher concentrations (e.g., greater than 10-15% by weight), the biomass slurries are not pumpable and/or stirrable and cause blockages in the reactor. It is desirable, however, to use higher concentrations of biomass slurries (e.g., 30-40% by weight) to reduce needed capital investment, lower variable costs due to improved extraction, and reduce water recycle.

The intermittent step of separating the solid and liquid fractions of the first reaction offers several advantages. The reduced viscosity of the first reaction mixture after the first reaction allows for easier separation of the solid fraction (comprising the majority of the lignin) and the liquid fraction (comprising the C6 and C5 sugars and oligomers or the C6 sugars and oligomers if the lignocellulosic biomass is pre-treated to remove a majority of the hemicellulose). If the viscosity were higher, it would be very difficult to separate the solid and liquid fractions (i.e., because a filter would rapidly clog and the flux would be very low).

The intermittent step of separating the solid and liquid fractions of the first reaction also was discovered to reduce or even prevent char formation. If lignin were not removed from the first reaction mixture, it would very rapidly convert to char and would render the resultant product unsuitable for use in high-end applications (e.g., resins, fine chemicals, etc.). Moreover, such char could bind or react with other target products (i.e., levulinic acid and furfural) to reduce the yield of these products. Thus, the above-described methods provide for improved recovery of lignin in the solid fraction of the first reaction mixture in form that is suitable for use in high-end applications.

Embodiments of the present description are further illustrated by the following examples, which are not to be construed in any way as imparting limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, quantities referred to by percentages (%) are by weight (wt %).

An exemplary embodiment of the above-described process compared the Biofine Process (see e.g., U.S. Pat. Nos. 4,897,497 and 5,608,105). The reaction parameters and processes are summarized in the table below.

|  | Example 1 | Comp. Ex. A (see Biofine) | Comp. Ex. B (see Biofine) |
| --- | --- | --- | --- |
| Biomass | softwood, 10 wt % | softwood, 30 wt % | softwood, 30 wt % |
| first reaction | 185° C., 90 sec, 5% | 185° C., 90 sec, 5% | 185° C., 90 sec, 5% |

-continued

|  | Example 1 | Comp. Ex. A (see Biofine) | Comp. Ex. B (see Biofine) |
| --- | --- | --- | --- |
| Liquefaction | $H_2SO_4$ | $H_2SO_4$ | $H_2SO_4$ |
|  | Yes | Yes | Yes |
| filtration step | Yes | No | No |
| concentration step | Yes | No | No |
| Scenario A | | | |
| second reaction | 175° C., 80 min, 5% $H_2SO_4$ | 175° C., 80 min, 5% $H_2SO_4$ | 175° C., 80 min, 5% $H_2SO_4$ |
| Char | No | Yes | No |
| Conversion | 95% | 95% | 55% |
| Selectivity | 60% | 60% | 40% |
| Yield | High | High | Low |
| levulinic acid concentration | High | Low | Low |
| Scenario B | | | |
| second reaction | 175° C., 240 min, 5% $H_2SO_4$ | 175° C., 240 min, 5% $H_2SO_4$ | 175° C., 240 min, 5% $H_2SO_4$ |
| Conversion | 100% | 100% | 95% |
| Selectivity | 40% | 40% | 25% |
| Char | No | Yes | Yes |
| yield LA | Lower than scenario A | Lower than scenario A | Very low |
| levulinic acid concentration | Lower than scenario A | Lower than scenario A | Lower than scenario A |

As can be seen from the foregoing, the intermittent step of separating the solid and liquid fractions of the first reaction mixture prevented the formation of char and increased the concentration of levulinic acid produced in the second reaction.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A method for liquefaction of a lignocellulosic biomass comprising:
   providing a lignocellulosic biomass slurry comprising a mineral acid in an amount from about 1% by weight to about 6% by weight;
   reacting the lignocellulosic biomass slurry at a first temperature of about 150° C. to about 200° C. for a first reaction period of about 30 seconds to about 10 minutes to produce a first reaction mixture, wherein the first reaction mixture has a reduced viscosity as compared to the lignocellulosic biomass slurry and is substantially free of levulinic acid and hydroxymethylfurfural; and
   separating the first reaction mixture into a solid fraction and a liquid fraction, the solid fraction comprising a majority of lignin from the lignocellulosic biomass slurry and the liquid fraction comprising a majority of hemicellulose and greater than about 30% by weight of cellulose from the lignocellulosic biomass slurry.

2. The method of claim 1, wherein the lignocellulosic biomass slurry comprises a pre-treated lignocellulosic biomass formed by extracting a majority of hemicellulose from the lignocellulosic biomass.

3. The method of claim 1, wherein the first reaction period is from about 30 seconds to about 5 minutes.

4. The method of claim 1, wherein the first reaction period is from about 60 seconds to about 5 minutes.

5. The method of claim 1, wherein the first reaction period is from about 60 seconds to about 120 seconds.

6. The method of claim 1, wherein the step of separating the first reaction mixture is performed when the first reaction mixture has a dry matter content of approximately 50% of that of the lignocellulosic biomass slurry before the first reaction.

7. The method of claim 1, wherein the first temperature is from about 160° C. to about 195° C.

8. The method of claim 1, wherein the first temperature is from about 165° C. to about 190° C.

9. The method of claim 1, wherein the first temperature is from about 175° C. to about 190° C.

10. A method for producing levulinic acid comprising the steps of:
    providing a lignocellulosic biomass slurry comprising a mineral acid in an amount from about 1% by weight to about 6% by weight;
    heating the lignocellulosic biomass slurry at a temperature of about 150° C. to about 200° C. for first reaction period of about 30 seconds to about 10 minutes to produce a first reaction mixture, wherein the first reaction mixture has a reduced viscosity as compared to the lignocellulosic biomass slurry and is substantially free of levulinic acid and hydroxymethylfurfural;
    separating the first reaction mixture into a solid fraction and a liquid fraction, the solid fraction comprising a majority of lignin from the lignocellulosic biomass slurry and a liquid fraction comprising a majority of hemicellulose and greater than about 30% by weight of cellulose originally present in the lignocellulosic biomass slurry; and
    reacting the liquid fraction at a temperature of about 120° C. to about 200° C. for a second reaction period sufficient to produce a second reaction mixture comprising levulinic acid and formic acid.

11. The method of claim 10, further comprising reacting the majority of hemicellulose extracted from the lignocellulosic biomass to produce furfural, levulinic acid, and/or formic acid.

12. The method of claim 10, further comprising reacting the solid fraction at a temperature and for a third reaction period sufficient to produce a third reaction mixture comprising levulinic acid and formic acid.

13. The method of claim 11, wherein the first reaction period is from about 30 seconds to about 5 minutes.

14. The method of claim 10, wherein the first reaction period is from about 60 seconds to about 5 minutes.

15. The method of claim 10, wherein the first reaction period is from about 60 seconds to about 120 seconds.

16. The method of claim 10, wherein the step of separating the first reaction mixture is performed when the first reaction mixture has a dry matter content of approximately 50% of that of the lignocellulosic biomass slurry before the first reaction.

17. The method of claim 10, wherein the first temperature is from about 160° C. to about 195° C.

18. The method of claim 10, wherein the first temperature is from about 165° C. to about 190° C.

19. The method of claim 10, wherein the method is effective to prevent formation of char or tar.

20. A method for liquefaction of a lignocellulosic biomass comprising:

reacting a lignocellulosic biomass slurry comprising about 1% by weight to about 6% by weight of a mineral acid at a temperature of about 150° C. to about 200° C. for a time period of about 30 seconds to about 5 minutes to produce a first reaction mixture; and separating the first reaction mixture into a solid fraction and a liquid fraction, wherein the solid fraction comprises greater than 50% by weight of lignin in the lignocellulosic biomass slurry, and wherein the liquid fraction comprises greater than 50% by weight of hemicellulose and greater than 30% by weight of cellulose in the lignocellulosic biomass slurry.

* * * * *